United States Patent [19]

Grollier

[11] Patent Number: 5,006,332
[45] Date of Patent: Apr. 9, 1991

[54] COMPOSITION FOR INDUCING AND STIMULATING THE GROWTH OF HAIR AND/OR RETARDING ITS LOSS, BASED ON AN AMPHOTERIC SURFACE-ACTIVE AGENT AND ON A PYRIMIDINE DERIVATIVE

[75] Inventor: Jean F. Grollier, Paris, France
[73] Assignee: L'Oreal, Paris, France
[21] Appl. No.: 365,803
[22] Filed: Jun. 14, 1989
[30] Foreign Application Priority Data Jun. 17, 1988 [LU] Luxembourg ............................ 87249

[51] Int. Cl.$^5$ ........................ A61K 7/075; A61K 7/06
[52] U.S. Cl. .............................. 424/70; 252/DIG. 13; 514/788
[58] Field of Search ................. 424/70; 252/DIG. 13; 514/788

[56] References Cited

U.S. PATENT DOCUMENTS 4,851,154  7/1989  Grollier et al. ........ 252/DIG. 13 X

FOREIGN PATENT DOCUMENTS 3615396  11/1987  Fed. Rep. of Germany .
WO88/01863  3/1988  PCT Int'l Appl. .

OTHER PUBLICATIONS

Alexander, "The Miranol Amphoteric Surfactants: Chemistry & Applications Part 2", 72 SPC—Soap, Perfumery & Cosmetics, 59 (1986) Nov., No. 11, London, Great Britain.

*Primary Examiner*—Thurman K. Page
*Assistant Examiner*—Susan S. Rucker
*Attorney, Agent, or Firm*—Fleit, Jacobson, Cohn, Price, Holman & Stern

[57] ABSTRACT

Washing and foaming composition for inducing and stimulating the growth of hair and/or retarding its loss, characterized in that it contains, in a physiologically acceptable medium, at least one amphoteric surface-active agent chosen from the amphocarboxyglycinates of formula:

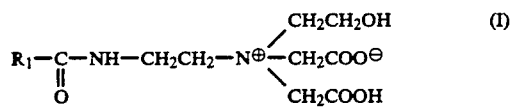

in which $R_1$ may denote an alkyl radical derived from copra, or a heptyl, nonyl or undecyl radical; and the amphocarboxypropionates corresponding to the formula:

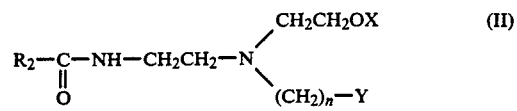

in which
n = 1 or 2,
X denotes —CH$_2$CH$_2$COOH, or hydrogen;
Y denotes —COOH or the radical

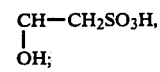

$R_2$ denotes an alkyl radical derived from copra, a saturated $C_7$, $C_9$, $C_{11}$ or $C_{13}$ alkyl radical, a $C_{17}$ alkyl radical and its iso form, a $C_{17}$ unsaturated radical, or an alkyl radical derived from linseed oil; as well as the physiologically acceptable salts of these compounds; and a pyrimidine derivative corresponding to the formula:

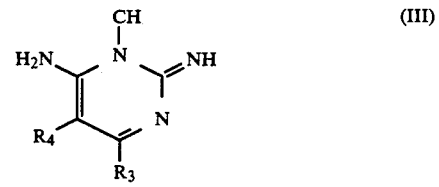

in which $R_3$ denotes a group

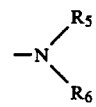

in which:
$R_5$ and $R_6$ are chosen from hydrogen, an alkyl group preferably containing 1 to 4 carbon atoms or an alkenyl, alkylaryl or lower cycloalkyl group;
$R_5$ and $R_6$ may also form a heterocyclic ring with the nitrogen atom to which they are bonded, this heterocyclic ring being chosen from aziridinyl, azetidinyl, pyrrolidinyl, piperidyl, hexahydroazepinyl, heptamethyleneimine, octamethyleneimine, morpholine and 4-(lower alkyl)piperazidinyl groups, it being possible for the heterocyclic groups to be substituted on the carbon atoms by one to three lower alkyl, hydroxyl or alkoxy groups;
the group $R_4$ is chosen from hydrogen, an alkyl, alkenyl, alkylalkoxy, cycloalkyl, aryl, alkylaryl, arylalkyl, alkylarylalkyl, alkoxyarylalkyl and lower haloarylalkyl group, as well as the salts of addition to physiologically acceptable acids.

19 Claims, No Drawings

COMPOSITION FOR INDUCING AND STIMULATING THE GROWTH OF HAIR AND/OR RETARDING ITS LOSS, BASED ON AN AMPHOTERIC SURFACE-ACTIVE AGENT AND ON A PYRIMIDINE DERIVATIVE

The present invention relates to a composition for inducing and stimulating the growth of hair and/or retarding its loss, containing, in combination, at least one pyrimidine derivative and at least one amphoteric surface-active agent.

For many years a search has been made in the cosmetics or pharmaceuticals industry for compositions which make it possible to eliminate or to reduce alopecia and especially to induce or to stimulate the growth of hair and/or to retard its loss.

With this in mind, compounds such as 6-amino-1,2-dihydro-1-hydroxy-2-imino-4-piperidinopyrimidine or minoxidil and its derivatives have already been proposed. Such compounds are described particularly in patent U.S. Pat. No. 4,139,619.

These compounds, and more particularly minoxidil, have been recommended for topical application to the scalp in the form of a lotion whose application is not followed by a rinse.

Furthermore, and bearing in mind the difficulties in dissolving these compounds, until now solvents have been employed, the effects of which on the hair of the people who are treated are in most cases hardly cosmetic, all the more since the recommended treatment requires several applications of the lotion at a daily frequency.

The term "hardly cosmetic" means a treatment which can make the hair adhere or make it sticky or greasy.

It appeared desirable and advantageous to investigate application of minoxidil by virtue of a surface-active solubilizing medium, that is to say a medium which is easily removed with water, such as, for example, a foaming solution or a shampoo which is applied to the scalp and wetted hair, which is optionally left in place for a few minutes after massaging and which is removed by rinsing with water.

This use would be all the more advantageous since the hair of individuals with a tendency to alopecia is frequently greasy and since it is desirable to employ a composition which washes, that is to say which frees the scalp and the hair from the secretions of sebum or other impurities which make hair sticky and which can impede the entry of the active agent, while at the same time depositing the quantity of active agents which is needed to act with regard to retarding hair loss and/or inducing and stimulating its fresh growth.

It has been thought to employ for this purpose surface-active agents which are relatively unreactive towards the scalp, particularly when the composition is left in place for some time before being rinsed off. Amphoteric surface-active agents may be mentioned among these surface-active agents.

The Applicant has found, however, that the stability with time of the pyrimidine derivatives, and in particular of minoxidil, in media of this kind was unsatisfactory.

The Applicant has found, in a surprising manner, that the problem of stability with time could be solved by virtue of the use of a particular group of amphoteric surface-active agents consisting of amphocarboxyglycinates or amphocarboxypropionates.

The compositions in accordance with the invention offer, therefore, the advantage of being particularly stable with time, essentially without any loss of active principle.

The subject of the present invention is, therefore, a composition intended to induce or stimulate the growth of hair and/or retard its loss, based on an amphoteric surface-active agent from the group of amphocarboxyglycinates or amphocarboxypropionates and pyrimidine derivatives.

Another subject of the invention consists of the process for treating hair and the scalp by virtue of a composition of this kind.

Other subjects of the invention will become apparent on reading the description and the examples which follow.

The composition forming the subject of the invention, intended for inducing and stimulating the growth of hair and retarding its loss, is characterized essentially by the fact that it contains, in a physiologically acceptable medium, at least one amphoteric surface-active agent chosen from amphocarboxyglycinates corresponding to the formula:

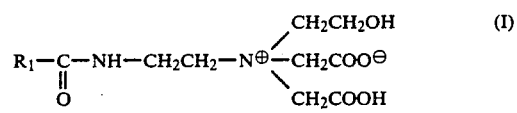 (I)

in which $R_1$ denotes an alkyl derivative derived from copra, a heptyl, nonyl or undecyl radical; or amphocarboxypropionates of formula:

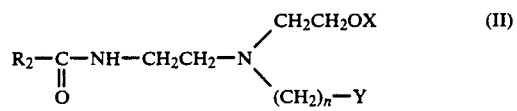 (II)

in which
n=1 or 2,
X denotes a $CH_2CH_2COOH$ radical or hydrogen,
Y denotes COOH or

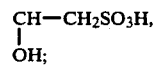

$R_2$ denotes an alkyl radical derived from copra, a saturated $C_7$, $C_9$, $C_{11}$, $C_{13}$, $C_{17}$ alkyl radical and the iso form, an unsaturated $C_{17}$ radical or an alkyl radical derived from linseed oil;
as well as their physiologically acceptable salts;
and at least one compound corresponding to the formula:

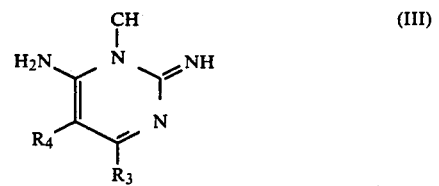 (III)

in which $R_3$ denotes a group

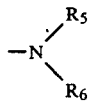

in which:

R$_5$ and R$_6$ are chosen from:

hydrogen, an alkyl group preferably containing 1 to 4 carbon atoms or an alkenyl, alkylaryl or lower cycloalkyl group;

R$_5$ and R$_6$ may also form a heterocyclic ring with the nitrogen atom to which they are bonded, this heterocyclic ring being chosen from aziridinyl, azetidinyl, pyrrolidinyl, piperidyl, hexahydroazepinyl, heptamethyleneimine, octamethyleneimine, morpholine and 4-(lower alkyl)piperazidinyl groups;

it being possible for the heterocyclic groups to be substituted on the carbon atoms by one to three lower alkyl, hydroxyl or alkoxy groups;

the group R$_4$ is chosen from hydrogen, an alkyl, alkenyl, alkoxyalkyl, cycloalkyl, aryl, alkylaryl, arylalkyl, alkylarylalkyl, alkoxyarylalkyl and lower haloarylalkyl group, as well as the salts of addition to cosmetically or pharmaceutically acceptable acids.

In formula (III) the alkyl or alkoxy groups preferably denote a group containing 1 to 4 carbon atoms; the alkenyl group preferably denotes a group containing 2 to 5 carbon atoms; the aryl group preferably denotes phenyl; the cycloalkyl group preferably denotes a group containing 4 to 6 carbon atoms.

The preferred compounds of formula (III) are chosen more particularly from the compounds in which R$_4$ denotes hydrogen and R$_3$ denotes a group:

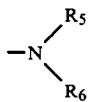

in which R$_5$ and R$_6$ form a piperidyl ring or else ethyl groups as well as their salts such as, for example, the sulphate.

Among these compounds, 6-amino-1,2-dihydro-1-hydroxy-2-imino-4-piperidinopyrimidine, also known as minoxidil, is particularly preferred.

Among the compounds which are particularly preferred, corresponding to formula (I) and defined above, use is made more particularly of the compounds of formula (I) in which R$_1$ denotes an alkyl radical derived from copra, and in particular the compound sold under the name Miranol C2M Conc., and referred to in the CTFA dictionary, 3rd edition, 1982, under the name "Cocoamphocarboxy-glycinate".

The preferred compounds of formula (II) are chosen more particularly from the compounds in which:

R$_2$ denotes an alkyl radical derived from copra
n=2
X=CH$_2$CH$_2$COONa
Y=COONa and more particularly the compound corresponding to formula (II), sold under the name Miranol C2M SF by the Miranol company and indicated in the CTFA dictionary, 3rd edition, 1982, under the name Cocoamphocarboxypropionate.

The salts of the compounds of formulae (I) or (II) are in particular salts of alkali metals such as sodium or of alkaline-earth metals.

A particularly preferred composition, in accordance with the invention, consists of a composition containing, in a physiologically acceptable medium, at least 6-amino-1,2-dihydro-1-hydroxy-2-imino-4-piperidinopyrimidine and an amphoteric surface-active agent of formula (I), in which R$_1$ denotes an alkyl radical derived from copra.

The compositions in accordance with the invention are washing and foaming compositions which, in addition to an excellent stability with time, exhibit no irritation of the scalp and leave the hair in a perfectly acceptable cosmetic state.

The compositions in accordance with the invention contain the pyrimidine derivative of formula (III) in proportions preferably of between 0.05 and 6% by weight relative to the total weight of the composition, and preferably between 0.1 and 3% by weight, and more particularly between 0.3 and 2% by weight.

The amphoteric surface-active agent of formulae (I) or (II) is preferably employed in proportions of between 1 and 30% by weight relative to the total weight of the composition, and preferably between 3 and 20%.

The physiologically acceptable medium may be a medium which is acceptable from the cosmetic or pharmaceutical viewpoint and may consist of an aqueous medium or a mixture of water and of a cosmetically or pharmaceutically acceptable solvent, optionally thickened.

The solvents employed may be particularly C$_1$-C$_4$ lower alcohols such as ethyl alcohol, isopropyl alcohol and tert-butyl alcohol; alkylene glycols such as propylene glycol and mono- and dialkylene glycol alkyl ethers such as ethylene glycol monoethyl ether, propylene glycol monomethyl ether and diethylene glycol monoethyl ether.

The solvents are preferably employed in proportions of between 0.5 and 10% by weight relative to the total weight of the composition.

These compositions may be thickened with thickening agents which are well known in the state of the art, and more particularly heterobiopolysaccharides such as xanthan gum or scleroglucans, cellulose derivatives, and acrylic polymers, crosslinked or otherwise.

These thickening agents are preferably employed in proportions of between 0.1 and 5% by weight relative to the total weight of the composition.

The compositions in accordance with the invention may also contain nonionic surface-active agents and more particularly agents chosen from polyhydroxypropyl ethers, polyoxyethylenated fatty alcohol ethers, oxyethylenated alkylphenols or mixtures of fatty alcohols and of polyoxyethylenated fatty alcohols, in proportions which may preferably go up to 10% by weight relative to the total weight of the composition.

The nonionic surface-active agents from the group of poly(hydroxypropyl ethers) are chosen more particularly from:

(1) the compounds of formula:

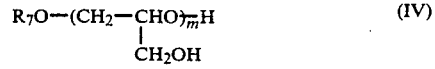  (IV)

in which R$_7$ denotes a radical or a mixture of alkyl radicals containing 10 to 14 carbon atoms and m is an integer or decimal number from 2 to 10, preferably from 3 to 6;

(2) the compounds of formula:

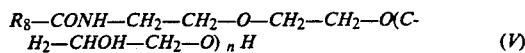

in which $R_8$ denotes a radical or a mixture of alkyl and/or alkenyl radicals containing from 11 to 17 carbon atoms and n denotes an integer or decimal number from 1 to 5 and preferably from 1.5 to 4;

(3) the compounds of formula:

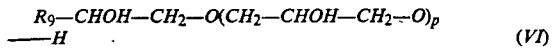

in which $R_9$ denotes an aliphatic, cycloaliphatic or arylaliphatic radical preferably containing 7 to 21 carbon atoms, and mixtures thereof, the aliphatic chains denoting in particular alkyl chains which may contain 1 to 6 ether, thioether and/or hydroxymethylene groups, and p is a number between 1 and 10 inclusive;

(4) the compounds prepared by acid-catalysed condensation of 2 to 10 and preferably of 2.5 to 6 moles of glycidol per mole of alcohol or of alpha-diol containing 10 to 14 carbon atoms;

(5) the compounds prepared by (poly)addition of glycerol monochlorohydrin to a poly(hydroxylated) organic compound in the presence of a strong base, and removal of water.

Nonionic surface-active agents which are more particularly preferred, in accordance with the invention, are chosen from:

(i) the polyhydroxypropyl ether compounds of formulae:

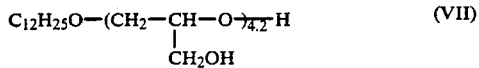

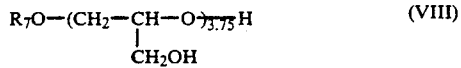

in which $R_7$ denotes a mixture of alkyl radicals $C_{10}H_{21}$ and $C_{12}H_{25}$.

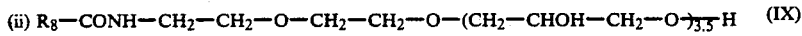

in which $R_8$ denotes a mixture of radicals comprising the following alkyl and alkenyl radicals: $C_{11}H_{23}$, $C_{13}H_{27}$, or radicals derived from copra fatty acids, or a radical derived from oleic acid;

(iii) the nonionic surface-active agent of the polyhydroxypropyl ether type, prepared by alkali-catalysed condensation of 3.5 moles of glycidol with a mixture of alpha-diols containing from 11 to 14 carbon atoms;

(iv) the compound of the polyhydroxypropyl ether type obtained by condensation of the monochlorohydrin (2.5 moles) with 1,2-dodecanediol in the presence of sodium hydroxide.

The nonionic surface-active agents of the polyethylene glycol ether group are chosen more particularly from the products of condensation of a mixture of fatty alcohols containing 10 to 22 carbon atoms with 1 to 24 moles of ethylene oxide.

The oxyethylenated alkylphenols are chosen more particularly from ($C_8$–$C_9$ alkyl)phenols oxyethylenated with 1 to 100 moles of ethylene oxide.

The mixtures of fatty alcohols and polyoxyethylenated fatty alcohols are chosen in particular from mixtures of $C_{10}$–$C_{22}$ fatty alcohols and $C_{10}$–$C_{22}$ alcohols oxyethylenated with 2 to 50 moles of ethylene oxide, in relative proportions of 10:90 to 90:10. By way of example, more particular mention may be made of the mixtures of 80% cetylstearyl alcohol and cetylstearyl alcohol oxyethylenated with 33 moles of ethylene oxide (20%).

The compositions in accordance with the invention may optionally contain ingredients which are traditionally employed in cosmetic or pharmaceutical compositions intended for a topical application and more particularly preserving agents, complexing agents, colorants, alkalifying or acidifying agents, perfumes and polymers.

The pH of these compositions is generally between 4 and 9 and preferably between 7 and 8.5.

They may be presented in the form of lotions, thickened or otherwise, gels, creams, emulsions, and may be pressurized in aerosol devices.

The compositions in accordance with the invention are intended more particularly to be employed for washing hair in shampoo form.

The treatment process for combating hair loss and/or stimulating its growth consists in applying the composition to wetted hair, in performing a massage, in optionally leaving it for a few minutes in contact with the hair, in rinsing with water and in optionally applying the shampoo another time, followed by a new rinsing with water.

The process in accordance with the invention exhibits the characteristics of a therapeutic treatment for alopecias insofar as the composition affects the biological mechanisms and especially the pilary cycle by correcting the dysfunction of the latter.

It also exhibits the characteristics of a cosmetic treatment, but at the same time it allows the hair and the scalp to be made more attractive.

The following examples are intended to illustrate the invention without, however, being limiting in nature.

EXAMPLE 1

A nonirritating, antiloss shampoo is prepared, of the following composition:

| | |
|---|---|
| Minoxidil | 0.25 g |
| Product called "Cocoamphocarboxyglycinate" (CFTA, 3rd edition, 1982), sold under the name Miranol C2M Conc. by Miranol in aqueous solution at a concentration of 38% of active substance | 15.0 g AS |
| Perfume, sequestrant q.s. | |
| Water q.s. | 100.0 g |

This shampoo exhibits an excellent stability with time without substantial loss of active principle (minoxidil).

EXAMPLE 2

A nonirritating, antiloss shampoo is prepared, of the following composition:

| | |
|---|---|
| Minoxidil | 0.25 g |
| Product called "Cocoamphocarboxy-glycinate" (CFTA, 3rd edition, 1982), sold under the name Miranol C2M Conc., by Miranol in aqueous solution at a concentration of 38% of active substance | 6.0 g AS |
| Perfume, sequestrant q.s. | |
| Water q.s. | 100.0 g |

This low-foam shampoo exhibits an excellent stability with time without substantial loss of active principle (minoxidil).

EXAMPLE 3

A shampoo for the treatment of hair loss is prepared, of the following composition:

| | |
|---|---|
| Minoxidil | 0.25 g |
| Compound of formula (II) in which: $R_2$ = undecyl, n = 2 $X = CH_2CH_2-COONa$ $Y = -COONa$ called "Lauroamphocarboxypropionate" (CTFA, 3rd edition, 1982), sold under the name Miranol H2M/SF Conc. by Miranol at the concentration of 39% of active substance (AS) | 15.0 g AS |
| Sequestrant | 0.2 g |
| Water q.s. | 100.0 g |

This shampoo has an excellent stability with time without loss of active principle.

EXAMPLE 4

A shampoo for the treatment of hair loss is prepared, of the following composition:

| | |
|---|---|
| Minoxidil | 0.26 g |
| Compound of formula (II) in which: $R_2$ = alkyl derived from copra n = 2 $X = -CH_2CH_2-COONa$ $Y = -COONa$ called "Cocoaamphocarboxypropionate" (CTFA, 3rd edition, 1982), sold under the name Miranol C2M/SF Conc. by Miranol at the concentration of 39% of active substance (AS) | 15.0 g AS |
| Sequestrant | 0.2 g |
| Water q.s. | 100.0 g |

This shampoo exhibits an excellent stability with time without loss of active principle.

EXAMPLE 5

A shampoo for the treatment of hair loss is prepared, of the following composition:

| | |
|---|---|
| Minoxidil | 0.25 g |
| Compound of formula (II) in which: $R_2$ = undecyl n = 1 X = H $Y = -\underset{\underset{OH}{\vert}}{CH}-CH_2-SO_3Na$ called "Lauroamphopropylsulphonate" (CTFA, 3rd edition, 1982), sold under the name Miranol HS Conc. by Miranol at the concentration of 38% of active substance (AS) | 15.0 g AS |
| Sequestrant | 0.3 g |
| Water q.s. | 100.0 g |

This shampoo exhibits an excellent stability with time without loss of active principle.

EXAMPLE 6

A shampoo for the treatment of hair loss is prepared, of the following composition:

| | |
|---|---|
| Minoxidil | 0.27 g |
| Sodium salt of the compound of formula (I) in which $R_1$ = undecyl called "Lauroamphocarboxyglycinate" (CTFA, 3rd edition, 1982), sold under the name Miranol H2M Conc. by Miranol at the concentration of 38% of active substance (AS) | 15.0 g AS |
| Sequestrant | 0.2 g |
| Water q.s. | 100.0 g |

This shampoo exhibits an excellent stability with time without loss of active principle.

EXAMPLE 7

A shampoo for the treatment of hair loss is prepared, of the following composition:

| | |
|---|---|
| Minoxidil | 0.27 g |
| Compound of formula (II) in which: $R_2$ = undecyl n = 1 X = H $Y = -COONa$ called "Lauroamphoglycinate" (CTFA, 3rd edition, 1982), sold under the name Miranol HM Conc. by Miranol at the concentration of 35% of active substance (AS) | 15.0 g AS |
| Sequestrant | 0.2 g |
| Water q.s. | 100.0 g |

This shampoo exhibits an excellent stability with time without loss of active principle.

EXAMPLE 8

A shampoo for the treatment of hair loss is prepared, of the following composition:

| | |
|---|---|
| Minoxidil | 0.25 g |
| Product called "Cocoamphocarboxyglycinate" (CTFA, 3rd edition, 1982), sold under the name Miranol C2M Conc. by Miranol in aqueous solution at a concentration of 38% of active substance (AS) | 3.8 g AS |
| Poly(hydroxypropyl ether) nonionic surfactant obtained by condensation of glycerol monochlorohydrin (2.5 moles) with 1,2-dodecanediol in the presence of sodium hydroxide according to French Patent FR-2,574,786 | 12.6 g |
| Sequestrant | 0.2 g |
| Water q.s. | 100.0 g |

I claim:

1. Washing and foaming composition for inducing and stimulating the growth of hair and/or retarding its loss, characterized in that it contains, in a physiologically acceptable medium, at least one amphoteric surface-active agent chosen from the amphocarboxyglycinates of formula:

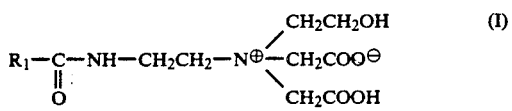

in which $R_1$ may denote an alkyl radical derived from copra, or a heptyl, nonyl or undecyl radical; and the amphocarboxypropionates corresponding to the formula:

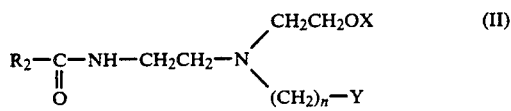

in which
$n = 1$ or 2,
X denotes —$CH_2CH_2COOH$, or hydrogen;
Y denotes —COOH or the radical

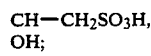

$R_2$ denotes an alkyl radical derived from copra, a saturated $C_7$, $C_9$, $C_{11}$, or $C_{13}$ alkyl radical, a $C_{17}$ alkyl radical and its iso form, a $C_{17}$ unsaturated radical, or an alkyl radical derived from linseed oil; as well as the physiologically acceptable salts of these compounds; and a pyrimidine derivative corresponding to the formula:

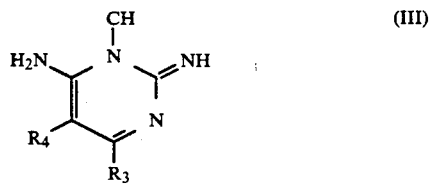

in which $R_3$ denotes a group

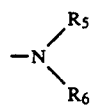

in which:
$R_5$ and $R_6$ are chosen from hydrogen, an alkyl group having 1 to 4 carbon atoms or an alkenyl, alkylaryl or lower cycloalkyl group;
$R_5$ and $R_6$ may also be from a heterocyclic ring with the nitrogen atom to which they are bonded, this heterocyclic ring being chosen from aziridinyl, azetidinyl, pyrrolidinyl, piperidyl, hexahydroazepinyl, heptamethyleneimine, octamethyleneimine, morpholine and 4-(lower alkyl)piperazidinyl groups, it being possible for the heterocyclic groups to be substituted on the carbon atoms by one to three lower alkyl, hydroxyl or alkoxy groups;
the group $R_4$ is chosen from hydrogen, an alkyl, alkenyl, alkylalkoxy, cycloalkyl, aryl, alkylaryl, arylalkyl, alkylarylalkyl, alkoxyarylalkyl and lower haloarylalkyl group, as well as the salts of addition to physiologically acceptable acids, wherein the pyrimidine derivative of formula (III) is present in proportions of between 0.05 and 6% by weight relative to the total weight of the composition, and wherein the amphoteric surface-active agent of formula (I) or (II) is present in proportions of between 1 and 30% by weight relative to the total weight of the composition.

2. Composition according to claim 1, wherein the pyrimidine derivative is a compound of formula (III) in which $R_4$ denotes hydrogen and $R_3$ denotes a group:

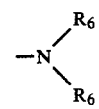

in which $R_5$ and $R_6$ form a piperidyl ring or else an ethyl group, as well as their physiologically acceptable salts.

3. Composition according to claim 1, wherein the amphocarboxyglycinate of formula (I) is a compound of formula (I) in which $R_1$ denotes an alkyl radical derived from copra.

4. Composition according to claim 1, wherein the amphocarboxypropionate of formula (II) is a compound in which:
$R_2$ denotes an alkyl radical derived from copra
$n = 2$
$X = CH_2CH_2COONa$
$Y = COONa$.

5. Composition according to claim 1, containing in a physiologically acceptable medium, at least 6-amino-1,2-dihydro-1-hydroxy-2-imino-4-piperidinopyrimidine and an amphoteric surface-active agent of formula (I) in which $R_1$ denotes an alkyl radical derived from copra.

6. Composition according to claim 1, wherein the pyrimidine derivative of formula (III) is present in the compositions in accordance with the invention in proportions of between 0.1 to 3% by weight.

7. Composition according to claim 1, wherein the amphoteric surface-active agent of formula (I) or (II) is present in the compositions in accordance with the invention in proportions of between 3 and 20% by weight.

8. Composition according to claim 1, further containing thickeners which are heterobiopolysaccharides, cellulose derivatives, acrylic polymers, crosslinked or otherwise, present in proportions of between 0.1 and 5% by weight relative to the total weight of the composition.

9. Composition according to claim 1, also containing preserving agents, complexing agents, colorants, alkalifying or acidifying agents, perfumes and polymers.

10. Composition according to claim 1, wherein the pH is between 4 and 9. Process for inducing and stimulating the growth of hair and/or retarding its loss, wherein a composition defined in claim 1 is applied to wetted hair, that a massage is performed, that it is left in contact for a few minutes, and it is rinsed off with water and that this composition is optionally applied another time, followed by a new rinsing.

11. Composition according to claim 1, wherein the physiologically acceptable medium is an aqueous medium or a mixture of water and of a cosmetically or pharmaceutically acceptable solvent, thickened or otherwise.

12. Composition according to claim 11, wherein the solvents are employed in proportions of between 0.5 and 10% by weight relative to the total weight of the composition.

13. Composition according to claim 1, additionally containing at least one nonionic surface-active agent.

14. Composition according to claim 13, wherein the nonionic surface-active agent is a polyhydroxypropyl ether, an ether of a polyoxyethylenated fatty alcohol, an oxyethylenated alkylphenol, and/or a mixture of fatty alcohols with polyoxyethylenated fatty alcohols.

15. Composition according to claim 14, wherein the nonionic surface-active agent of the polyhydroxypropyl ether type is:

(i) the compounds of formula:

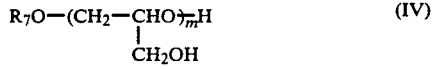

(IV)

in which $R_7$ denotes a radical or a mixture of alkyl radicals containing 10 to 14 carbon atoms and m is an integer or decimal number from 2 to 10;

(ii) the compounds of formula:

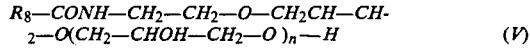

(V)

in which $R_8$ denotes a radical or a mixture of alkyl and/or alkenyl radicals containing from 11 to 17 carbon atoms, and n denotes an integer or decimal number from 1 to 5;

(iii) the compounds of formula:

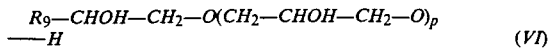

(VI)

in which $R_9$ denotes an aliphatic, cycloaliphatic or arylaliphatic radical preferably containing 7 to 21 carbon atoms and mixtures thereof;

(iv) the compounds prepared by acid-catalysed condensation of 2 to 10 and preferably of 2.5 to 6 moles of glycidol per mole of alcohol or of alpha-diol, containing 10 to 14 carbon atoms;

(v) the compounds prepared by (poly)addition of glycerol monochlorohydrin to a poly(hydroxylated) organic compound in the presence of a strong base and removal of water.

16. Composition according to claim 14, wherein the polyethylene glycol ether is a product of condensation of fatty alcohols containing 10 to 22 carbon atoms with 1 to 24 moles of ethylene oxide.

17. Composition according to claim 14, wherein the oxyethylenated alkylphenol is a ($C_8$–$C_9$ alkyl)phenol oxyethylenated with 1 to 100 moles of ethylene oxide.

18. Composition according to claim 14, wherein the mixture of fatty alcohols and of polyoxyethylenated fatty alcohols is a mixture of $C_{10}$–$C_{22}$ fatty alcohols and $C_{10}$–$C_{22}$ fatty alcohols oxyethylenated with 2 to 50 moles of ethylene oxide.

19. Process for inducing and stimulating the growth of hair and/or retarding its loss, wherein a composition defined in claim 1 is applied to wetted hair, that a massage is performed, that it is left in contact for a few minutes, and it is rinsed off with water and that this composition is optionally applied another time, followed by a new rinsing.

* * * * *